(12) United States Patent
Schildkraut et al.

(10) Patent No.: US 11,331,059 B2
(45) Date of Patent: May 17, 2022

(54) METHOD FOR LOCAL X-RAY BONE DENSITY TOMOGRAPHY

(71) Applicants: Jay S. Schildkraut, Rochester, NY (US); Subramanyan Krishnamoorthy, Palatine, IL (US); Jean-Marc Inglese, Bussy-Saint-Georges (FR)

(72) Inventors: Jay S. Schildkraut, Rochester, NY (US); Subramanyan Krishnamoorthy, Palatine, IL (US); Jean-Marc Inglese, Bussy-Saint-Georges (FR)

( * ) Notice: Subject to any disclaimer, the term of this patent is extended or adjusted under 35 U.S.C. 154(b) by 0 days.

(21) Appl. No.: 16/641,475

(22) PCT Filed: Aug. 27, 2018

(86) PCT No.: PCT/US2018/048111
§ 371 (c)(1),
(2) Date: Feb. 24, 2020

(87) PCT Pub. No.: WO2019/040932
PCT Pub. Date: Feb. 28, 2019

(65) Prior Publication Data
US 2021/0153823 A1      May 27, 2021

Related U.S. Application Data

(63) Continuation-in-part of application No. PCT/US2018/048080, filed on Aug. 27, 2018.

(60) Provisional application No. 62/550,089, filed on Aug. 25, 2017.

(51) Int. Cl.
| A61B 6/14 | (2006.01) |
| A61B 6/02 | (2006.01) |
| A61B 6/00 | (2006.01) |
| A61B 6/03 | (2006.01) |

(52) U.S. Cl.
CPC ............... *A61B 6/14* (2013.01); *A61B 6/025* (2013.01); *A61B 6/032* (2013.01); *A61B 6/4085* (2013.01); *A61B 6/4241* (2013.01); *A61B 6/461* (2013.01); *A61B 6/505* (2013.01); *A61B 6/5217* (2013.01)

(58) Field of Classification Search
CPC ......... A61B 6/14; A61B 6/5217; A61B 6/032; A61B 6/505; A61B 6/4241; A61B 6/025; A61B 6/4085; A61B 6/461; A61B 6/482; A61B 6/469; G06T 11/008; G16H 50/30; G16H 30/40
See application file for complete search history.

(56) References Cited

U.S. PATENT DOCUMENTS 9,848,818 B1 * 12/2017  Kopperdahl ........... A61B 5/055

* cited by examiner

*Primary Examiner* — Courtney D Thomas

(57) ABSTRACT

A method for characterizing bone structure for a patient, method executed at least in part on a computer, acquires one or more 2D x-ray projection images of a volume, wherein image content is acquired at two or more spectral frequencies. The acquired x-ray image content is processed to calculate one or more metrics that characterize bone structure within the imaged volume. The one or more calculated metrics are displayed.

23 Claims, 11 Drawing Sheets

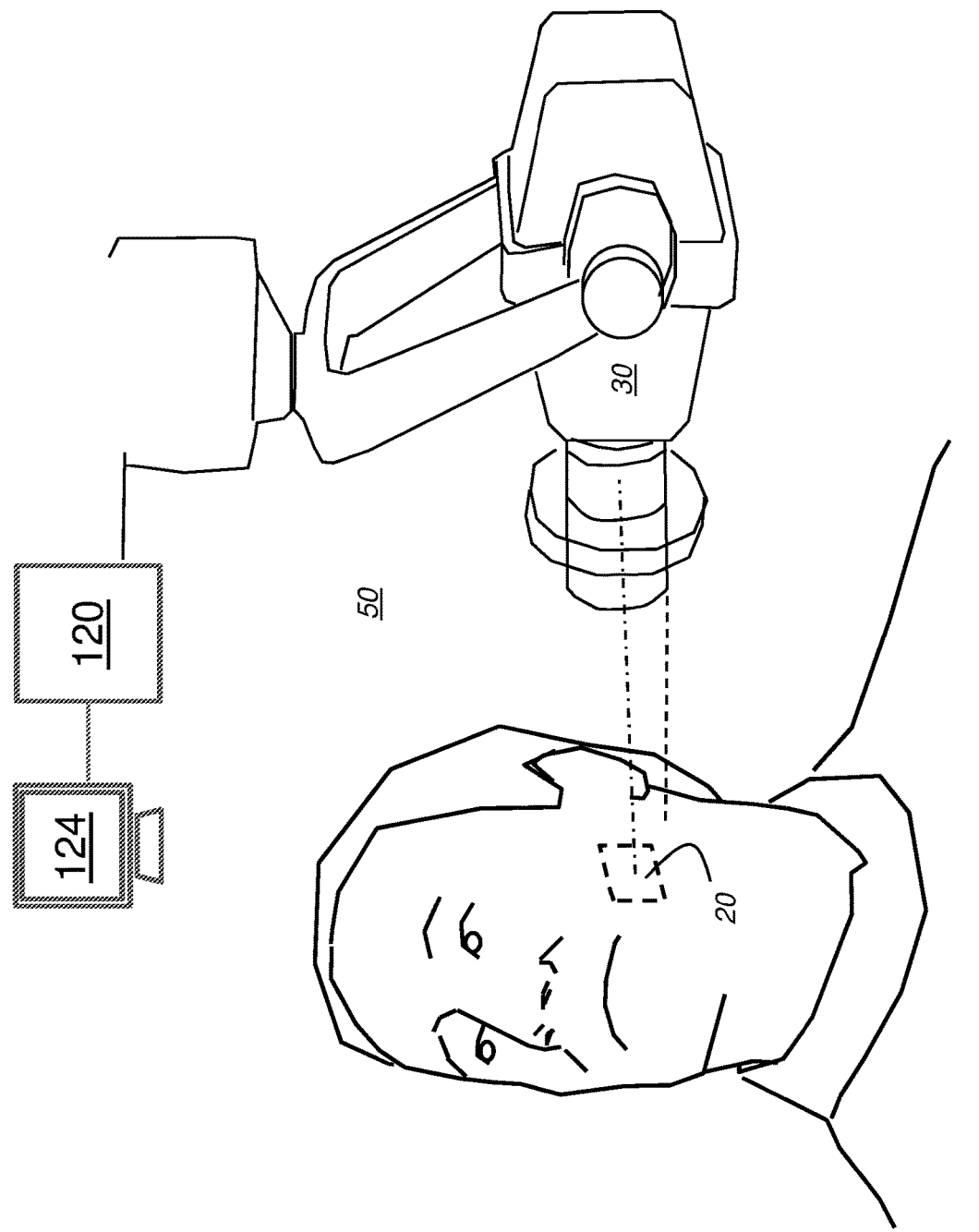

METHOD FOR LOCAL X-RAY BONE DENSITY TOMOGRAPHY

CROSS REFERENCE TO RELATED APPLICATIONS

This application claims the benefit of International Patent Application No. PCT/US2018/048080 filed on Aug. 27, 2018 and entitled "METHOD FOR LOCAL X-RAY BONE DENSITY TOMOGRAPHY", which is incorporated herein in its entirety by this reference, and claims the benefit of U.S. Provisional Application Ser. No. 62/550,089 filed on Aug. 25, 2017 and entitled "METHOD FOR LOCAL X-RAY BONE DENSITY TOMOGRAPHY", which is incorporated herein in its entirety by this reference.

FIELD OF THE INVENTION

The disclosure relates generally to the field of X-ray imaging and more particularly to dental apparatus and methods using X-ray scans to determine mineral density of bonelike tissue.

BACKGROUND OF THE INVENTION

The determination of bone mineral density (BMD) and tooth mineral density are of significant value in dentistry. For example, a missing tooth can be replaced with an implant that requires the insertion of a post into the mandible bone or the maxillary bone. The determination of bone density enables improved or optimal implant placement. Tooth mineral density is important for the assessment of overall tooth health. The demineralization of tooth enamel is an early indication of tooth decay.

Dual-Energy X-ray absorptiometry (DXA) uses two-dimensional (2D) projection radiographs acquired with two different energy distributions to determine the areal bone density of regions of interest of the skeletal anatomy, including the spine, femur, and forearm, for example (see "Dual Energy X Ray Absorptiometry for Bone Mineral Density and Body Composition Assessment," International Atomic Energy Agency Human Health Series No. 15, 2010).

Quantitative computed tomography (QCT) is a three-dimensional (3D) X-ray imaging technique that is able to quantify bone density. QCT may use a single X-ray energy distribution to obtain a 3D image with accurate Hounsfield units or attenuation coefficients that can provide bone density. QCT may also use two or more X-ray source distributions or energy discriminating detectors to determine material type and composition. In QCT, an object is scanned with a well calibrated CT scanner. For each captured scan (projection) $I_0$, the X-ray exposure at each detector pixel, in the absence of the object, is known. The projections are corrected for scatter, by using Monte Carlo calculations for example, to determine the X-ray scatter caused by the object and by other material in the X-ray system. The calculated scatter is removed from the measured projections. In addition, corrections are made to the projections to compensate for non-ideal detector characteristics. QCT is described further in "Quantitative CT for the determination of mineral density: a review," by C. E. Cann, Radiology Vol. 166 (1988).

While both DXA and QCT have found wide clinical applications for bone density determination for skeletal anatomy, these methods have limitations that preclude their use in dental applications. In general, conventional DXA is poorly suited for dental imaging because DXA uses 2D projection radiography that is unable to distinguish overlapping tissue. QCT, when applicable, especially in the multi-spectral case, provides detailed bone density information. Unfortunately, it is difficult to use QCT in dental clinical applications in which only a small volume-of-interest (VOI) of a patient, that is, only a portion of the full head, is imaged. With a small VOI, the whole scanned object cannot be fully reconstructed, which makes it impossible to fully correct for scatter, beam hardening, and other physical processes that must be taken into consideration in order to produce a quantitative CT scan.

Conventional QCT methods obtain averaged information that helps to characterize bone density for teeth and for many types of bone structures. However, because the QCT method generates averaged values from bulk volume density that provide no characterization of bone structure, the computed BMD value lacks sufficient local scale information for diagnostic assessment of trabecular bone.

Trabecular bone has a complex structure formed of tiny, irregularly spaced lattice-shaped units (trabeculae). Also termed "spongy bone", trabecular bone forms central portions of the alveolar process, providing the socket structures that seat the teeth, for example. Trabecular bone structure is quantified over a volume of bone in terms of a trabecular bone score (TBS). By comparison with BMD metrics that average bulk density values of pixels/voxels within imaged bone, TBS metrics characterize local bone structure as evidenced by bone texture. In TBS techniques, variations along the bone mass are sampled from individual pixels/voxels outward, using localized measurement of trabecular thickness and gradient features to provide, among other aspects, a measure of bone strength and an assessment of relative robustness of the bone for ability to withstand stress and weight, for support of implants, and for other characteristics.

In particular dental applications, TBS shows promise for assessing whether or not a portion of the jaw can provide sufficient structural support for an implant or other apparatus. Implant stability for initial placement as well as for the success of subsequent osseointegration depends in large part upon having suitable trabecular bone structure. Unlike the BMD, which quantifies averaged bone density for the bone mass, the TBS characterizes the local structure of that portion of the jaw in which an implant is placed. Thus, a combination of both BMD and TBS information yields a more accurate characterization of bone health and indicator of implant success.

For these reasons, it can be appreciated that there would be value in imaging methods that can obtain both accurate bone mineral data (BMD) and trabecular bone structure (TBS) characterization for dental implants and other procedures related to patient dentition.

SUMMARY OF THE INVENTION

An aspect of the present disclosure is to advance the art of dental imaging with particular interest in providing a quantitative assessment of bone mineral density for the teeth.

It is an object of the present disclosure to provide 3D images that include the measurement of the mineral density of bone-like tissue where only a local volume-of-interest (VOI) (e.g., small VOI) of a patient is imaged. Bone-like tissue includes, but is not intended to be limited to, alveolar bone, teeth, cortical bone, trabecular bone, and/or any mineral containing tissue.

Another aspect of the present disclosure is to address, in whole or in part, at least the foregoing and other deficiencies in the related art. For example, unlike conventional DXA, density information using exemplary embodiments of the present disclosure is three-dimensional, reducing or overcoming disadvantages for BMD measurement due to overlapping tissue. Further, exemplary embodiments of the present disclosure address situations for which conventional QCT is not applicable because only a small VOI of the patient can be fully reconstructed into a 3D image. Further advantages can be obtained by apparatus and methods that can allow combined BMD and trabecular bone structure information to be acquired.

It is another aspect of the present disclosure to provide, in whole or in part, at least the advantages described herein.

These objects are given only by way of illustrative example, and such objects may be exemplary of one or more embodiments of the disclosure. Other desirable objectives and advantages inherently achieved by the may occur or become apparent to those skilled in the art. The invention is defined by the appended claims.

According to an aspect of the present disclosure, there is provided a method for characterizing bone structure for a patient, the method executed at least in part on a computer and comprising:

a) acquiring one or more 2D x-ray projection images of a volume, wherein image content is acquired at two or more spectral frequencies;

b) processing the acquired x-ray image content to calculate one or more metrics that characterize bone structure within the imaged volume; and c) displaying the one or more calculated metrics.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation.

FIG. 11 shows an embodiment of an intraoral apparatus for spectral imaging.

DESCRIPTION OF EXEMPLARY EMBODIMENTS

Figure 1:
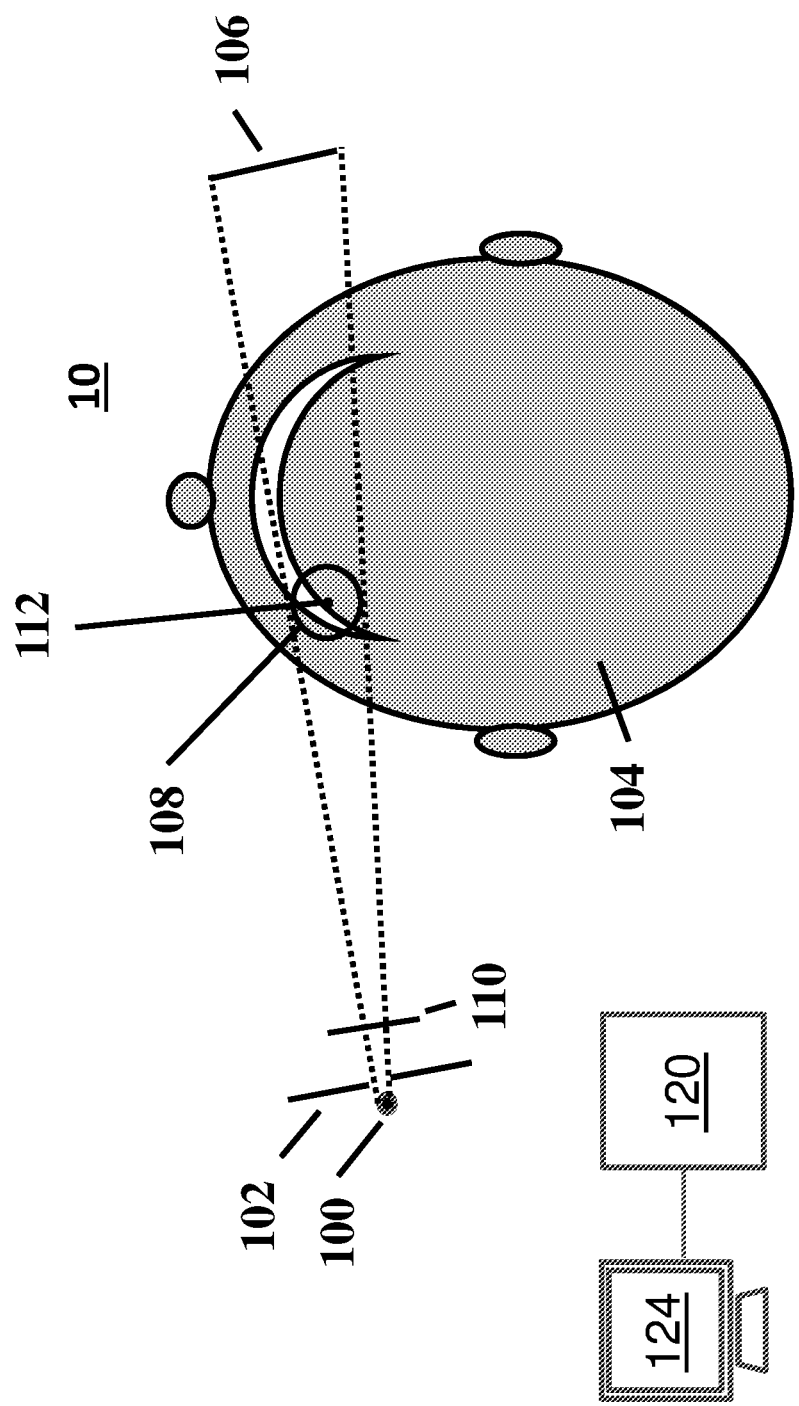
FIG. 1 is a schematic diagram of a dental imaging system for performing an x-ray scan of a patient for generating a 3D volume reconstruction of a portion of the patient according to the present disclosure.

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

The term "exemplary" indicates that the description is used as an example, rather than implying that it is an ideal. The terms "subject" and "object" may be used interchangeably to identify the object of a dental apparatus or the subject of an image.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

In dental applications, it is generally desirable to scan only a limited VOI in order to limit radiation exposure to the patient. When a VOI is scanned, the acquired X-ray projections are considered to be truncated, meaning that all projections may not contain the whole of the scanned object. As used herein, a "VOI" is the part of the scanned object that is contained in all projections. The remainder of the scanned object is contained in only a subset of projections, and therefore cannot be fully reconstructed.

In the context of the present disclosure, the region surrounding or near to the VOI includes the volume of the object that is contained in not all, but in a significant fraction of the projections (such as at least half). This part of the object can usually be reconstructed with a high degree of accuracy.

Certain exemplary method and/or apparatus embodiments according to the present disclosure use known material within a VOI to determine local conditions within the VOI and as an aid to determining mineral density of bone-like tissue in the VOL Tissue or other material of known composition is referred to as "prior" material because the composition of the "prior" material is known before the X-ray scan. Specifically, exemplary embodiments according to the present disclosure use prior material within a VOI to provide an indication of the local spectral distribution of X-rays in the acquired scan so that the density of adjacent bone-like material can be determined.

According to an exemplary embodiment of the present disclosure, soft tissue is used as the "prior" material because soft tissue has a mineral density of zero and often surrounds bone-like tissue. However, exemplary method and/or apparatus embodiments according to the present disclosure include using any material of known composition in (e.g., completely or partially within) or around the VOI in the determination of mineral density of bone-like tissue in the VOI (e.g., near the known material). Accordingly, as used herein, material of known composition or "prior" material can include, but not be limited to, naturally occurring tissue, material that has been added such as crowns, and/or material that is inserted into the object volume for the duration of the scan.

Certain exemplary method and/or apparatus embodiments according to the present disclosure use automatic segmentation and classification of known material inside and/or outside the VOI in order to facilitate determination of the bone-like tissue's mineral density.

Certain exemplary method and/or apparatus embodiments according to the present disclosure may use spectral X-ray imaging to aid in the segmentation process and in density determination for bone-like material.

Spectral X-ray imaging is performed with two or more X-ray sources with different energy spectra or energy resolving detectors with two or more energy bins.

In selected exemplary embodiments described herein, the known BMD of gums, as soft tissue, is zero. Using this soft tissue as the prior material, a reference is established; processing can then calculate the unknown BMD of neighboring bone-like tissue. However, exemplary method and/or apparatus embodiments are intended to include the use of tissue or material having any known mineral density or composition as a prior material.

As used in the present description, the voxel values in a reconstruction are referred to as attenuation coefficients. It is common practice to convert these values to Hounsfield units, using well known conversion factors. Exemplary embodiments according to the present disclosure include using Hounsfield units to denote voxel values.

FIG. 1 shows an X-ray source or X-ray source focal spot 100 of a dental imaging apparatus 10 irradiating patient 104. Imaging apparatus 10 can be a cone-beam computed tomography (CBCT) apparatus, for example. The X-ray source 100 can be collimated by collimator 102 so that only the X-rays are limited to the area of a detector 106 of the dental imaging apparatus 10. The X-rays can also pass through a filter 110 before entering the patient. When an X-ray scan is acquired, the X-ray source 100, the collimator 102, the filter 110, and the detector 106 are moved around the patient. Typically, the X-ray source 100 is moved in a 360 degree circle around a fixed point 112, which is often referred to as the isocenter or axis of rotation (AOR). Generally, for 3D image reconstruction, the X-ray source and detector need to traverse a scan of at least 180 degrees plus a fan beam angle. A volume-of-interest (VOI) 108 is the volume that is irradiated by the X-ray source 100 at all source focal spot locations of the X-ray scan. The VOI 108 can be fully reconstructed into a 3D image, whereas the region of the patient 104 outside of this VOI 108 can only be partially reconstructed, and generally with distorted geometry.

Exemplary embodiments according to this application can use other types of X-ray scans including scans in which the source 100 moves in a partial circle, which is often referred to as a "short scan." Axis AOR may also move during exemplary scans, for example, to enlarge the VOI. The AOR may move in one direction, in two directions, or in 3 dimensions during exemplary scans, for example, to irradiate the VOI 108. Exemplary embodiments according to the present disclosure are also intended to include the use of a stationary X-ray source or sources with multiple focal spots (e.g., carbon nanotube (CNT) X-ray source). Specifically, exemplary embodiments herein preferably apply to any X-ray scan in which a volume-of-interest (VOI) is substantially reconstructed because the VOI 108 is irradiated over a suitably large range of source locations, but wherein a significant portion of the object (e.g., patient 104) cannot be sufficiently reconstructed. For example, exemplary embodiments of the present disclosure are intended to include tomosynthesis in which the object (e.g., VOI 108) is scanned using a more limited range of source angles, but using high resolution detectors.

A control logic processor 120 is in signal communication with detector 106 and with control circuitry (not shown) for coordinating radiation emission and data acquisition and processing. A display 124 can then provide display of the reconstructed VOI as well as displaying calculated values for BMD and other useful data, including information that can be helpful for assessment and diagnosis.

In certain exemplary method and/or apparatus embodiments according to the present disclosure, X-ray images with different spectral distributions are used. For example, the excitation voltage of the X-ray source 100 can be changed between low and high values during a single scan (e.g., fast switching). In addition, the filter may also be changed along with the voltage. Alternatively, two or more separate scans may be performed with different spectra from a single X-ray source. In exemplary embodiments according to the present disclosure, it may be useful to employ more than one X-ray source and detector.

Another exemplary embodiment uses a single X-ray source having a broad spectral bandwidth and a detector that is able to distinguish X-ray energy. For example, a photon counting detector with two or more energy bins can preferably be used as a detector capable of distinguishing X-ray energy.

Figure 2:
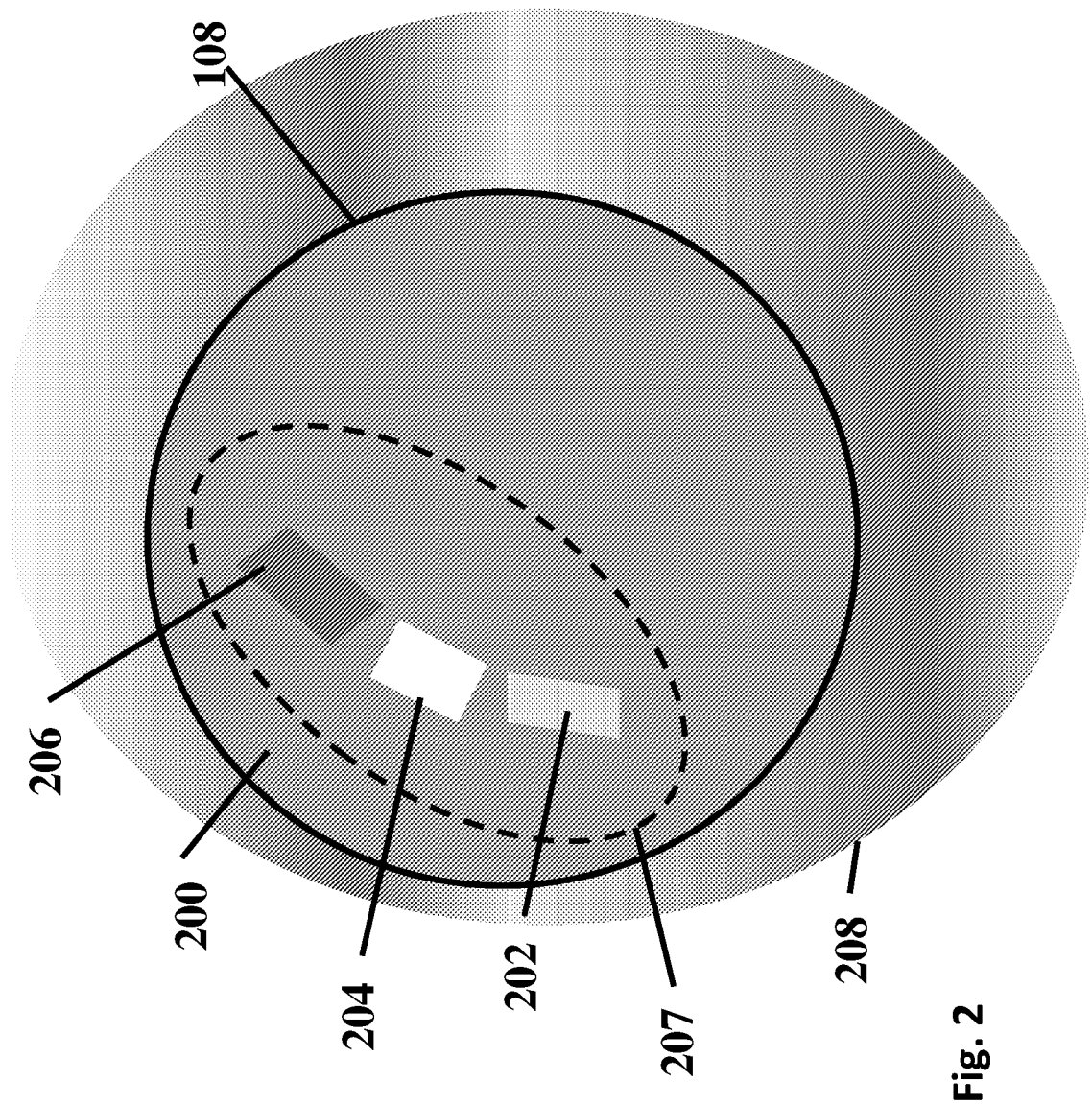
FIG. 2 is a schematic diagram that shows additional detail of the VOI 108 according to an exemplary embodiment of the present disclosure.

FIG. 2 is a schematic diagram that shows a 2D perspective view with additional detail of the VOI 108 according to an exemplary embodiment of the present disclosure. As shown in FIG. 2, a portion of the scanned patient's head region 208 outside the VOI 108 is generally poorly imaged. Content in this region 208 is geometrically distorted and the size and boundary of the head of the patient 104 is substantially unknown. For example, the VOI 108 for dental imaging is often about 5×5×5 cm$^3$ (125 cm$^3$) in size, whereas a head of the adult patient 104 has a volume of about 3000 cm$^3$. Therefore, an exemplary VOI embodiment contains less than 5% of a typical human head. Inside the VOI 108, there is soft tissue (ST) 200 and bone-like tissue 202, 204, and 206 of varying mineral density. The region bounded by a dashed line shows prior voxels 207. The prior voxels need not include all of the non-bone-like voxels inside the VOI. Only voxels that are classified as a type with a known composition are included among the prior voxels 207. As shown in FIG. 2, the prior voxels 207 include soft tissue (ST) 200 near or surrounding each of the bone-like tissue of varying mineral density 202, 204, and 206.

For the purpose of describing certain exemplary method and/or apparatus embodiments herein, the human head, both inside and outside of the VOI, is preferably modeled as a combination of soft tissue (ST) and hydroxyapatite (HA). The definition of soft tissue may vary. For the purpose of describing exemplary embodiments herein, the soft tissue 200 characterization as described by the International Commission on Radiological Protection, Publication 100 (ICRP100) is used. However, other definitions of soft tissue could be used and can be applied in exemplary embodiments herein. Soft tissue (ST) represents a combination of lipid, water, muscle, and other soft tissue that is found in a body (e.g., human body). From the aspect of radiological imaging, soft tissue has negligible mineral content.

For the purpose of describing exemplary embodiments herein, bone-like tissue mineral content (e.g., bone-like tissue of varying mineral density 202, 204, and 206) is preferably modeled by the mineral hydroxyapatite (HA). However, definition of bone-like tissue mineral content may vary. The density ρ at every point in the object has a density value that is a summation of the density of ST and HA, respectively $\rho_{ST}$ and $\rho_{SA}$, multiplied by a weighting factor as shown in equation (1):

$$\rho = f_{ST}\rho_{ST} + f_{HA}\rho_{HA} \qquad (1)$$

wherein factors $f_{ST}$ and $f_{HA}$ are fractional values for soft tissue and hydroxyapatite, respectively, as defined in more detail subsequently.

Using the model expressed in equation (1), the X-ray attenuation coefficient μ at every point in the object is given by equation (2), $$\mu = \rho(f_{ST}\hat{\mu}_{ST} + f_{HA}\hat{\mu}_{HA}) \qquad (2)$$

wherein $\hat{\mu}_{ST}$ and $\hat{\mu}_{HA}$ are the mass attenuation coefficients of ST and HA, respectively.

One useful object of exemplary embodiments herein is to determine $f_{HA}$ for bone-like tissue in the VOI 108.

Note that if the whole object, such as the entire mandible bone and the entire maxillary bone, were scanned with a monochromatic X-ray source, beam hardening is not a concern. A standard reconstruction method such as filtered back projection would produce accurate attenuation coefficients (assuming that scatter correction and detector calibration is performed). When the entire object is scanned with the monochromatic X-ray source, $f_{HA}$ can be easily determined using the additional assumption in equation (3).

$$f_{ST} + f_{HA} = 1 \qquad (3)$$

If the object is scanned with two X-ray spectra (dual-energy) or additional X-ray spectra, then the equation (3) constraint can be relaxed, since more data is available for density measurement.

X-ray sources that are used in diagnostic medical and dental imaging are polychromatic, which results in beam hardening caused by the energy dependence of the attenuation coefficient of all materials. If beam hardening can be corrected, as it is in conventional QCT practice, then factor $f_{HA}$ can again be determined.

Exemplary embodiments herein address situations in which the X-ray source(s) is polychromatic and wherein only a VOI, and not the full volume, can be fully reconstructed. The inability to reconstruct the compete object reduces or prevents full beam hardening correction from being performed because the material that the X-rays pass through outside the VOI (and therefore the extent of the X-ray spectrum) is unknown.

Single-Spectra Embodiments for BMD Characterization

Figure 3:
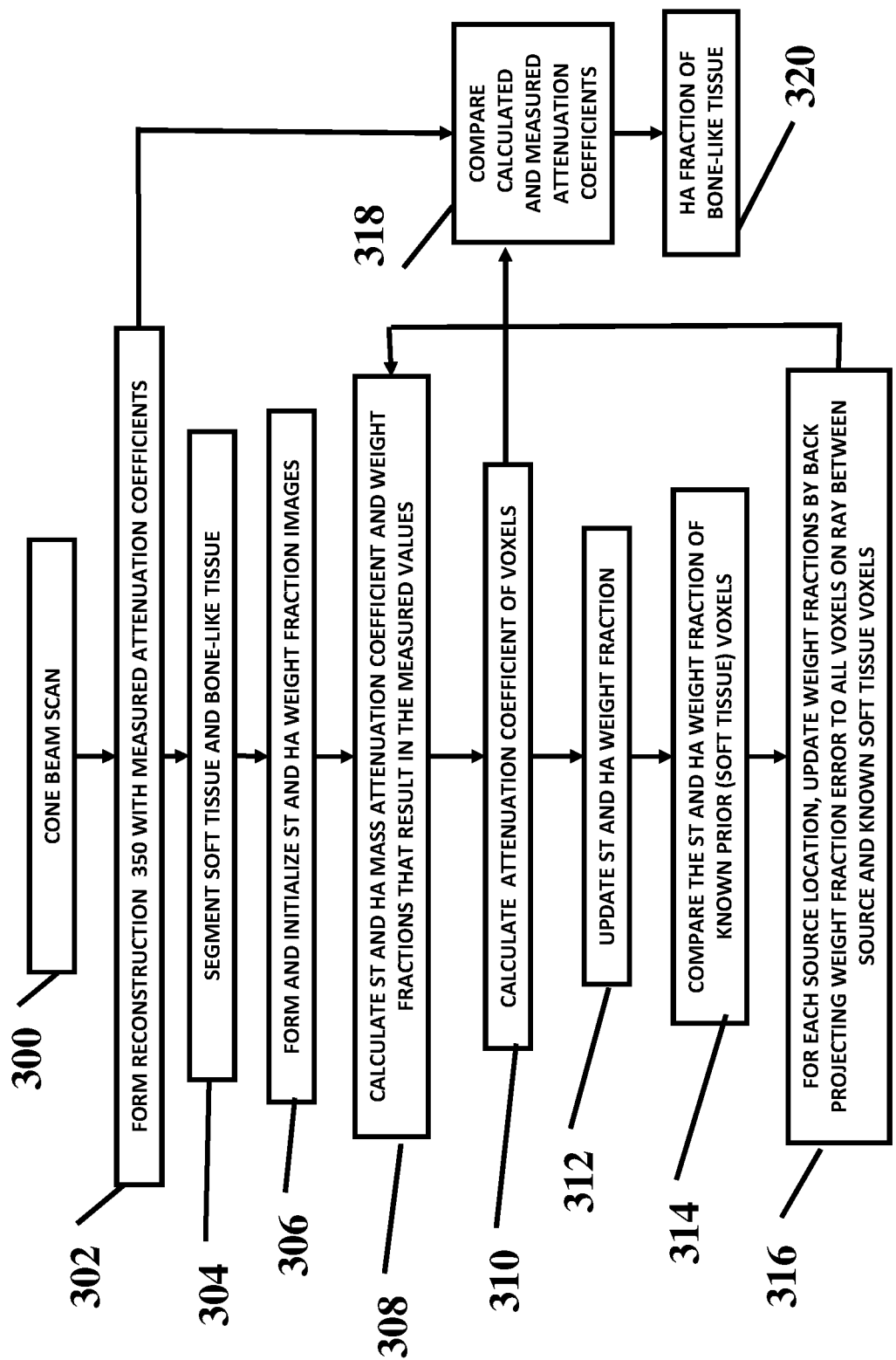
FIG. 3 is a flow chart that shows one exemplary method embodiment according to the present disclosure.

FIG. 3 is a flow chart that shows one exemplary method embodiment for computing attenuation coefficients according to the present disclosure. As shown in FIG. 3, measured projection images from scanning by the dental X-ray imaging apparatus 10 of VOI 108 are acquired in an acquisition step 300. The measured projection images are processed to create a reconstruction 350 in a reconstruction step 302. Reconstruction 350 includes not only the VOI, but also a volume that is large enough to contain the whole of the scanned object within the head of the patient 104. In general and in FIG. 3, the voxel values of the reconstruction are proportional to X-ray attenuation coefficients. Using an ideal detector, in the absence of object truncation, scatter, and beam hardening, the voxel values are the product of density times mass attenuation coefficient of the object. Under typical conditions, however, the voxel values in reconstruction 350 (including the reconstructed VOI) are not sufficiently accurate for derivation of X-ray attenuation coefficients. Thus, the subsequent remaining process steps of the method embodiment of FIG. 3 are used or are required to enable the recovery of more accurate density information for bone-like tissue contained in the VOI of the scanned object.

Reconstruction 350 in step 302 is preferably generated using methods/apparatus that remove scatter from the measured projections. Exemplary scatter correction can include removing a constant amount of scatter from each projection, scatter removal based on Monte Carlo calculations, scatter estimation that is based on the content of the projects such as the PEP model, or other suitable method of scatter correction.

The reconstruction method in step 302 can use filtered back-projection (FBP). Alternatively, algebraic reconstruction (ART) has the advantage of producing a reconstruction for which calculated projections, which are produced by forward projection through the reconstruction, match the measured projections. This is a useful consideration for exemplary method and/or apparatus embodiments herein because, outside of the VOI, the reconstruction 350 is distorted. However, exemplary ART techniques can produce reconstructions with accurate density x-path length values that are used in subsequent steps of the sequence given in the flow chart of FIG. 3.

In a segmentation step 304, soft tissue and bone-like tissue in the VOI of reconstruction 350 are segmented. In this exemplary embodiment, it is only necessary to segment a material of known composition and density in the VOI of reconstruction 350. In FIG. 3, the known material, which serves as a "prior", can be soft tissue or some other tissue or material having a known composition and known mineral density. The prior material is a subset of the reconstruction voxels, wherein each member of the subset has a known density value. Conventional segmentation method/apparatus can be used to identify this subset of voxels in step 304. For example, segmentation can be applied as described in commonly assigned U.S. Pat. No. 8,761,493 entitled "Method and system for tooth segmentation in dental images" to Chen et al.; U.S. Pat. No. 8,929,635 entitled "Method and system for tooth segmentation in dental images" to Chen et al.; and U.S. Pat. No. 9,129,363 entitled "Method for teeth segmentation and alignment detection in CBCT volume" to Chen et al., each of which is herein incorporated by reference in its entirety.

Other suitable segmentation techniques can include, but are not limited to, K-mean segmentation, levels set segmentation, and segmentation using snakes. Exemplary segmentation methods are described in "Various Image Segmentation Techniques: A Review," by Dilpreet Kaur et al., *International Journal of Computer Science and Mobile Computing*, Vol. 3 Issue. 5, May-2014, pg. 809-814; "A Review on image processing and image segmentation," by J. Kuruvilla, D. Sukumaran, A. Sankar and S. P. Joy, 2016 *International Conference on Data Mining and Advanced Computing (SAPIENCE)*, pp. 198-203; and "Automated medical image segmentation techniques" by Sharma N and Aggarwal L M. *Journal of Medical Physics/Association of Medical Physicists of India*. 2010; 35(1):3-14, all of which are hereby incorporated by reference in their entirety.

The soft tissue that is obtained by segmentation in step 304 is preferably used as a "prior". This means that the soft tissue serves as the tissue of known composition, having a mineral density that is typically zero. The exemplary processing sequence of FIG. 3 thus identifies soft tissue with zero mineral density as the prior. However, alternate exemplary method and/or apparatus embodiments according to the present disclosure can use any material with known composition, and thus known density, as a "prior". In an alternate embodiment, a known material, such as a material that is foreign to the body that serves as the object of the imaging process, can be inserted inside or placed near the VOI and within the field of view of the imaging system to serve as a "prior". At the conclusion of step 304, a subset of the voxels of the VOI are labeled as prior.

Continuing with the FIG. 3 sequence, following segmentation step 304, one or two weight fraction images are generated in a fraction image forming step 306. Each fraction image has the same dimensions and number of voxels as the reconstructed 3D image; the fraction images are useful data structures for the iterative processing computations that follow. As processing progresses, the fraction image values for a voxel more accurately indicate the relative density and composition of the material represented by that voxel.

In step 306, a 3D HA fraction image, having the same size as the VOI reconstruction, is formed for the purpose of storing the computed HA fraction at each voxel. If the condition in equation (3) is not applicable, then a 3D ST fraction image is also formed. The HA fraction image and the ST fraction images just formed are then both initialized. For example, for voxels that are not labeled as prior, the HA fraction is set to 0.0 and the ST fraction to 1.0. For voxels that are identified as prior, the ST and HA fractions are set to their known value from the reconstruction.

Next, in a calculation step 308, the ST and HA mass attenuation coefficient is calculated at each voxel and a new value of $f_{ST}$ and $f_{HA}$ fractions for each voxel is calculated.

Figure 4:
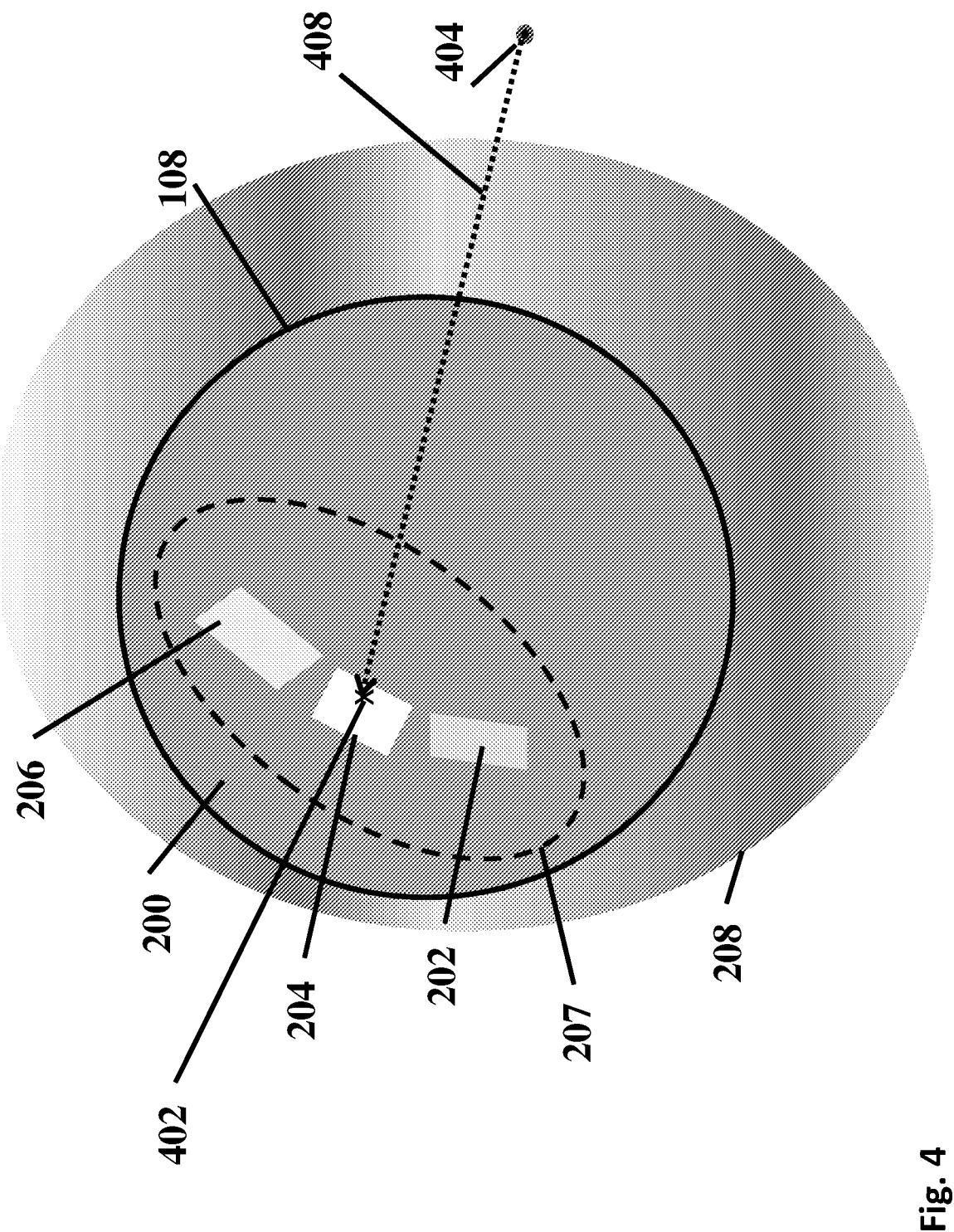
FIG. 4 is a diagram that shows exemplary mass attenuation coefficient determination in the VOI.

FIG. 4 is a diagram that shows exemplary mass attenuation coefficient determination in the VOI 108. As shown in FIG. 4, a voxel 402 is shown with an X-ray 408 from a source focal spot 404 to the voxel. As X-rays propagate from focal spot 404 to voxel 402 (e.g., through air and through part of the patient 104), the spectrum of the X-rays changes. This X-ray spectrum change is often referred to as "beam hardening." The X-ray spectrum, and therefore the mass attenuation coefficient of ST and HA at voxel 402, depend on the value of $f_{ST}$ and $f_{HA}$ at all voxels along X-ray 408. If the focal spot 404 is described as the i'th focal spot and the index j is used to denote successive voxels along the X-ray 408, then the ST and HA mass attenuation coefficients at the voxel 402 in step 308 of the FIG. 3 sequence have the form of equations (4) and (5), $$\hat{\mu}_{HA}^i = \Gamma\left(\sum_j f_{HA}^j, \sum_j f_{ST}^j\right) \qquad (4)$$

$$\hat{\mu}_{ST}^i = \Gamma\left(\sum_j f_{HA}^j, \sum_j f_{ST}^j\right) \qquad (5)$$

where the function $\Gamma$ can be pre-calculated and depend on the spectrum and the path length.

The effective ST and HA mass attenuation coefficient computed for a voxel is the mass attenuation value of equations (4) and (5) averaged over all N X-ray source focal spot locations i in the X-ray scan as set forth in equations (6) and (7).

$$\hat{\mu}_{ST} = \frac{1}{N}\sum_1^N \hat{\mu}_{ST}^i \qquad (6)$$

$$\hat{\mu}_{HA} = \frac{1}{N}\sum_1^N \hat{\mu}_{HA}^i \qquad (7)$$

With respect to the FIG. 3 sequence, in an effective attenuation coefficient calculation step 310, the effective mass attenuation coefficient is calculated for each voxel, for voxels both inside and outside the VOI using the above equations (6) and (7). The calculated values are compared with the values in the reconstruction 350 in a comparison step 318.

In an update step 312 new values of weight fractions $f_{ST}$ and $f_{HA}$ are calculated using equation (3) and equations (8) and (9):

$$f_{HA}^{Calc} = (\mu_{recon}/\rho - \hat{\mu})/(\hat{\mu}_{HA} - \hat{\mu}_{ST}) \qquad (8)$$

The value of $f_{HA}$ is updated for all voxels using equation (9):

$$f_{HA}^{New} = \alpha(f_{HA}^{Calc} - f_{HA}^{Current}) + f_{HA}^{Current} \qquad (9)$$

wherein $\alpha$ is an empirically determined constant which is smaller than 1.0. Value $\mu_{recon}$ is the attenuation value generated using the reconstructed voxel.

Constraints are then applied to the iterative process of mineral density determination of FIG. 3 in comparison and update steps 314 and 316. Application of local constraints for the exemplary method embodiment of FIG. 3 is significant since the VOI is substantially smaller than the whole object and the whole object cannot be accurately recovered using the scanned projections. Using local constraint data, tissue in the neighborhood of prior voxels can have its mineral density determined to within some level of accuracy.

In comparison step 314 of FIG. 3, the current value of $f_{ST}$ and $f_{HA}$ is compared to the known values for prior voxels that were identified as prior in step 304. In update step 316, the error of the current and known value is back-projected to update the value $f_{ST}$ and $f_{HA}$ for voxels that lie on a ray between the prior voxel and the focal spot. This process is preferably repeated for each prior voxel for all focal spot locations that comprise the scan of step 300.

Following update step 316, control returns to step 308 and processing iterates until conditions in comparison step 318 are satisfied. The calculated attenuation coefficient must be close to the value in the reconstruction 350, and the values of $f_{ST}$ and $f_{HA}$ for the prior voxels must be close to their known values.

Computed results for bone mass density and data related to the calculations used to generate BMD values are displayed to the practitioner or other viewer in a display step 320.

Dual-Energy Embodiments for BMD Characterization

As described herein, exemplary alternate method and/or apparatus embodiments according to the present disclosure can use scans having two or more energy spectra or a single scan with a detector that can resolve the excited photons into two or more energy bins. Preferably, the energy resolving detector counts incident photons.

Figure 5:
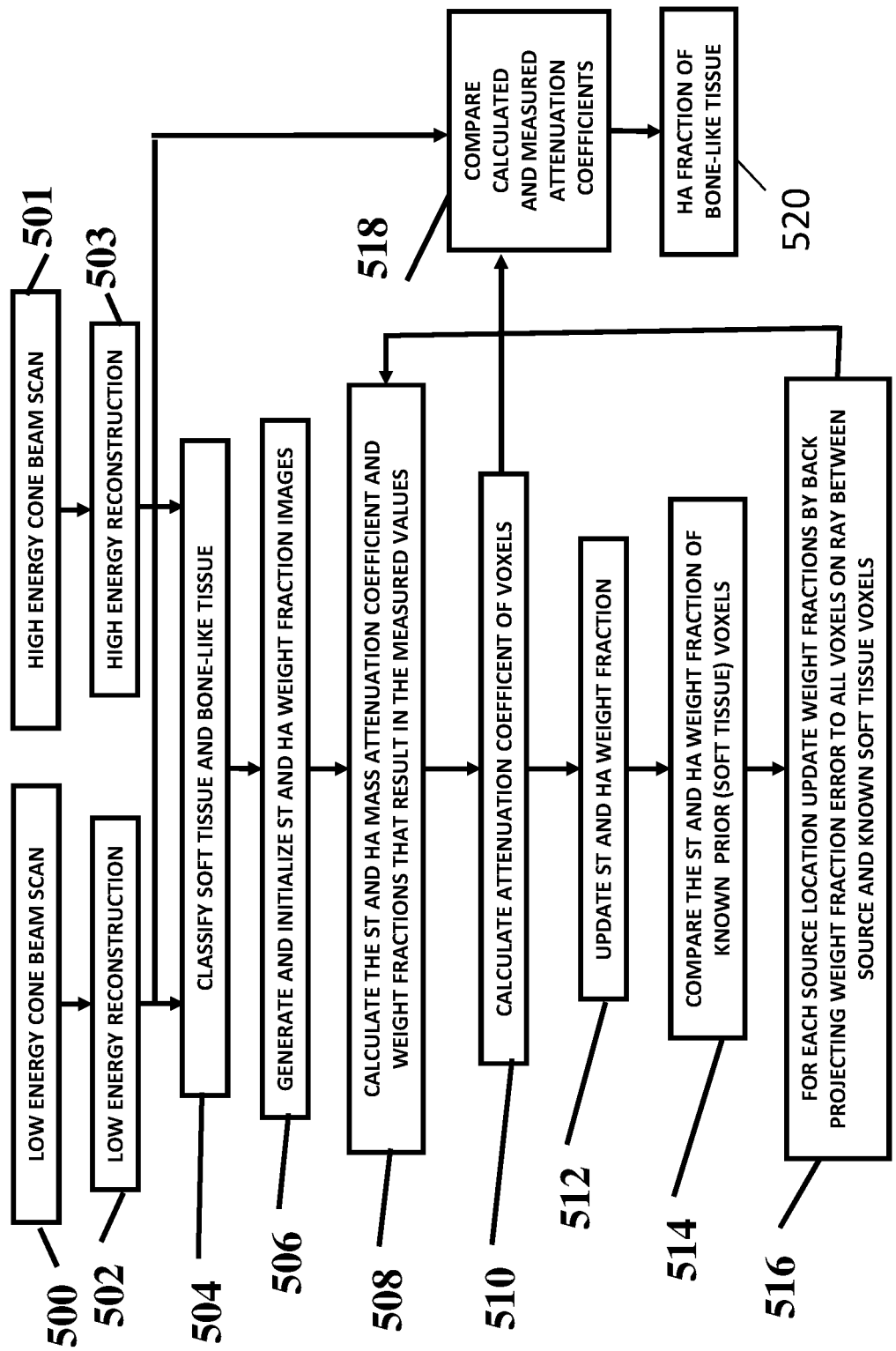
FIG. 5 is a flow chart that shows one exemplary dual spectrum method embodiment according to the present disclosure.

FIG. 5 is a flow chart that shows an exemplary dual spectrum method embodiment according to the present disclosure. As shown in FIG. 5, the exemplary dual spectrum method embodiment uses a combination of low energy and high energy scans. In respective acquisition steps 500 and 501, a low and high energy X-ray spectrum scan are acquired. For example, the scans can be captured with different peak voltage (kVp) applied to the X-ray source. Also, the high energy scan can have added source filtration in order to reduce the spectral overlap of the low and high X-ray source spectra. In respective reconstruction steps 502 and 503, measured projection images from the low and high energy scans are reconstructed to form a corresponding low energy scan reconstruction and a high energy scan reconstruction.

"Prior" material is identified in the VOI in the vicinity of the bone-like material for which mineral density is to be determined in a classification step 504. Step 504 is improved relative to the analogous step 304 in the single source spectrum method embodiment shown in FIG. 3. The availability of low and high energy reconstructions transforms step 504 from an image segmentation operation or technique to an image classification operation or technique. Image segmentation methods may still be applied as in step 304, but soft tissue enhanced and bone-like material enhanced reconstructions improve the segmentation results in step 504.

Conventional image classification methods can be used including but not limited to those described in S. S. Nath, G. Mishra, J. Kar, S. Chakraborty and N. Dey, "A survey of image classification methods and techniques," 2014 *International Conference on Control, Instrumentation, Communication and Computational Technologies (ICCICCT)*, Kanyakumari, 2014, pp. 554-557 and "*Techniques in Image Classification; A Survey*" by S. V. S. Prasad, T. Satya Savithri and Iyyanki V. Murali Krishna, in the *Global Journal of Researches in Engineering: Electrical and Electronics Engineering*, Vol. 15 Issue 6 2015, all of which are hereby incorporated by reference in their entirety.

Referring again to the FIG. 5 sequence, in a fraction images initialization step 506, the ST weight fraction image $f_{ST}$ and HA weight fraction image $f_{HA}$ are initialized. Since, in the multi-spectrum case, more information is captured as compared with single spectrum imaging, the condition in equation. (3) need not be applied. As a result, the ST and HA fractions can be calculated independently.

In a calculation step 508, the ST and HA mass attenuation coefficient is calculated at each voxel for both the low energy spectrum reconstruction and the high energy spectrum reconstruction. ST and HA weight fractions $f_{ST}$ and $f_{HA}$ are also calculated. These values are used in a subsequent calculation step 510 along with the current values of $f_{ST}$ and $f_{HA}$ to calculate the low and high spectrum attenuation coefficient for all voxels. These calculated attenuation coefficients are used in the comparison between calculated and measured attenuation coefficients in a subsequent comparison step 518.

In an update step 512, new weight fractions are calculated for all voxels using the low and high energy spectrum. In the case that equation (3) is applied, since $f_{HA}$ must have the same value for both spectra, a weighted average of the value that is calculated using the low and high energy spectrum value is used as set forth in equation (10):

$$f_{HA}{}^{Calc} = (\mu_{recon}^{L,H}/\rho - \hat{\mu}_{ST}^{L,H})/(\mu_{HA}^{L,H} - \hat{\mu}_{ST}^{L,H}) \tag{10}$$

Alternatively, dual-energy scans allow both $f_{ST}$ and $f_{HA}$ to be independently calculated for their respective scans using equations (11) and (12):

$$f_{HA}^{Calc} = \frac{1}{\rho}(\mu_{recon}^{H}\hat{\mu}_{ST}^{L} - \mu_{recon}^{L}\hat{\mu}_{ST}^{H})/(\hat{\mu}_{ST}^{L}\hat{\mu}_{HA}^{H} - \hat{\mu}_{ST}^{H}\hat{\mu}_{HA}^{L}) \tag{11}$$

$$f_{ST}^{Calc} = \frac{1}{\rho}(\mu_{recon}^{L}\hat{\mu}_{HA}^{H} - \mu_{recon}^{H}\hat{\mu}_{HA}^{L})/(\hat{\mu}_{ST}^{L}\hat{\mu}_{HA}^{H} - \hat{\mu}_{ST}^{H}\hat{\mu}_{HA}^{L}) \tag{12}$$

Preferably, the weight fractions are only partially updated to a new value as in equation (9) to reduce or prevent the likelihood that the iterative process in FIG. 5 becomes unstable or stops at a local minimum.

The current weight fractions of prior voxels of known composition are compared in a comparison step 514. In this exemplary embodiment, prior voxels of known composition are soft tissue. In comparison step 514, the comparison uses voxels that were classified as soft tissue for which $f_{ST}=1$ and $f_{HA}=0$. In an update step 516, the weight fraction error is back-projected to update the values at voxels that lay between each prior voxel and a source focal spot for the low energy and high energy scans. Similar to FIG. 3, steps 514 and 516 locally constrain the iterative method of mineral density determination for bone-like tissue to produce correct values for voxels that were classified as a known material that are located near the bone-like tissue. This local constraint enables the exemplary dual spectrum method embodiment to produce correct weight fractions for the bone-like tissue.

In comparison step 518, the known weight fractions of prior voxels are compared with calculated values, and calculated attenuation coefficients are compared with values in the reconstructions. When calculated and measured values are satisfactorily close, the iterative calculation in FIG. 5 ends at step 518 and the composition of the bone-like material at each voxel is obtained. In a calculation step 520, the HA fraction at each voxel 520 is produced.

Exemplary embodiments according to the present disclosure can use scans at two or more X-ray spectra and/or detectors that are able to resolve X-rays into two or more energy bins to determine relative values of X-ray attenuation coefficients. As described herein, when the scanned VOI is smaller than the scanned object, the use of relative values can be superior to using absolute values in the determination of the mineral density of bone-like tissue. Exemplary embodiments according to the present disclosure include using ratios, differences, and any other relative value of attenuation coefficients or Hounsfield units in the determination of the mineral density of bone-like tissue in the VOI. For the purpose of describing one exemplary embodiment, the ratio of the low and high energy reconstruction is defined in equation (13) as:

$$R \equiv \frac{\mu^L}{\mu^H} \tag{13}$$

Also, the ratio of ST and HA mass attenuation coefficients for the low and high energy scan are defined below in equations (14)-(17) as:

$$\hat{R}_{ST} \equiv \frac{\hat{\mu}_{ST}^L}{\hat{\mu}_{ST}^H} \tag{14}$$

$$\hat{R}_{HA} \equiv \frac{\hat{\mu}_{HA}^L}{\hat{\mu}_{HA}^H} \quad (15)$$

$$\hat{R}_{HA/ST}^L \equiv \frac{\hat{\mu}_{HA}^L}{\hat{\mu}_{ST}^L} \quad (16)$$

$$\hat{R}_{HA/ST}^H \equiv \frac{\hat{\mu}_{HA}^H}{\hat{\mu}_{ST}^H} \quad (17)$$

where the ^symbol is used to denote the mass attenuation coefficient.

Figure 6:
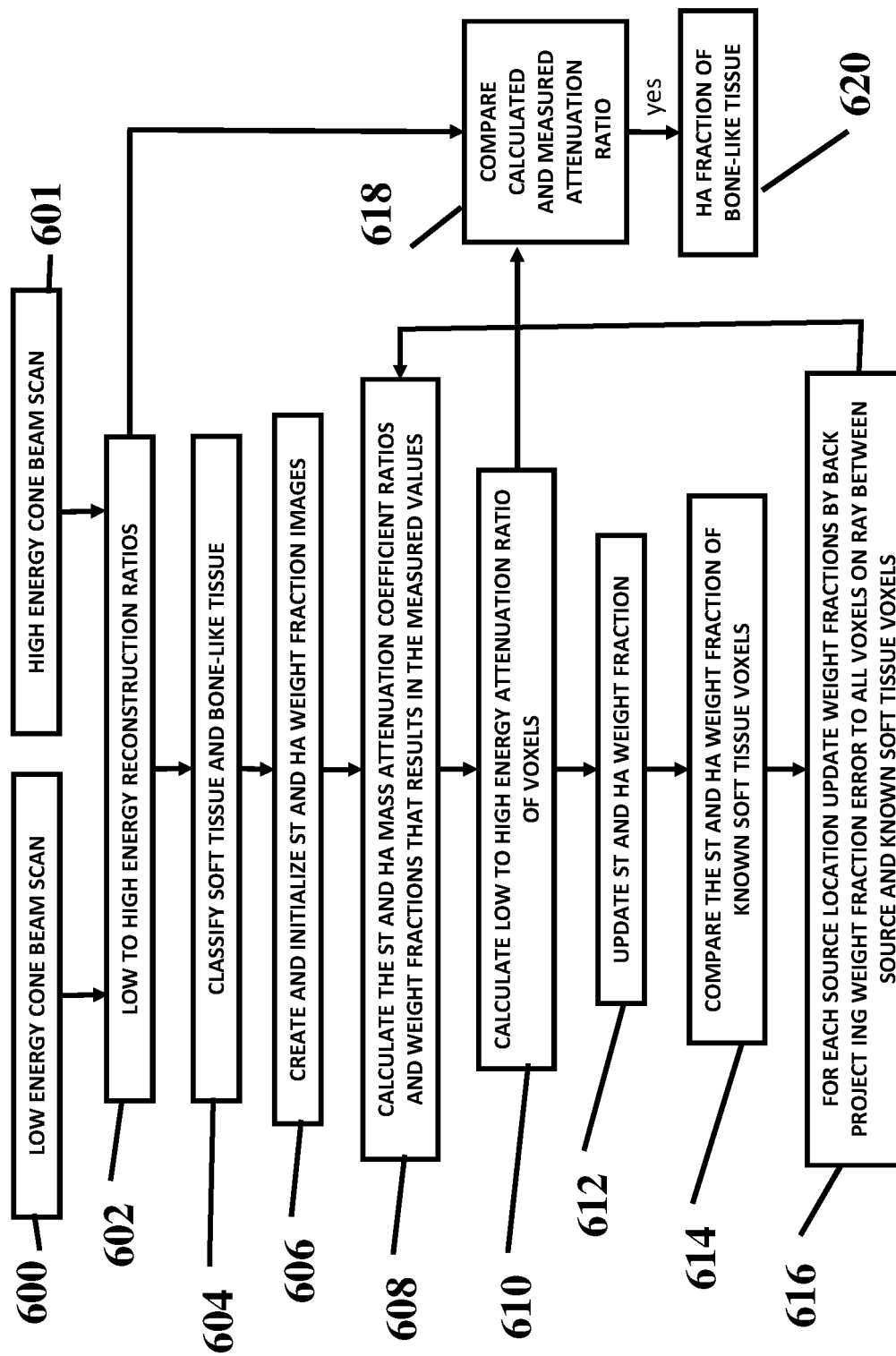
FIG. 6 is a flow chart that shows an alternate dual spectrum method embodiment according to the present disclosure.

FIG. 6 is a flow chart that shows an exemplary dual spectrum method embodiment according to an alternate embodiment of the present disclosure that uses relative values of X-ray attenuation coefficients in determining the mineral density of bone-like tissue (e.g., in the VOI) in the scanned object. As shown in FIG. 6, in respective acquisition steps 600 and 601, a low and high energy X-ray spectrum scan of the object are acquired. In a calculation step 602, the low energy to high energy reconstruction ratio (e.g., in equation (13)) is calculated.

In a classification step 604, this ratio is used in the classification of material of known composition and at least bone-like tissue material in the reconstructions. In a VOI scan in which the captured projections are truncated, absolute values of attenuation coefficients are unreliable for use in image classification because values depend on the amount of truncation and the location of the VOI in the object (e.g., the head). The use of relative values can improve the segmentation and classification process of step 604.

In a fraction images initialization step 606, the ST and HA weight fraction at each voxel is initialized. Then in a calculation step 608, the ST and HA mass attenuation ratios in equations (14) to (17) are calculated at each voxel. In a calculation step 610, the attenuation ratio is calculated, and then in a subsequent comparison step 618, the calculated attenuation ratio is compared with the measured value from the reconstructions, which was calculated in step 602.

In an update step 612, new values of $f_{ST}$ and $f_{HA}$ are calculated. When equation (3) is applied the equation (18), $$f_{HA}^{Calc} = \frac{1}{1 + \hat{R}_{HA/ST}^H \left( \frac{\hat{R}_{HA} - R}{R - \hat{R}_{ST}} \right)} \quad (18)$$

is used to calculate a new value of $f_{HA}$. The current weight fractions are updated using equation (9). In respective comparison and update steps 614 and 616, the weight fractions are updated to reduce the error between the calculated and known weight fractions of the prior (e.g., classified as soft tissue) voxels. Control then jumps back to step 608 until comparison step 618 determines that the prior voxels have a correct weight fraction and the calculated attenuation ratios matches (e.g., closely matches) the ratios in step 602, and then the exemplary method embodiment of FIG. 6 ends. When the decision in step 618 is affirmative and the method ends, the result is the output of the determined mineral density of the bone-like tissue of the VOI in calculation step 620.

Characterizing Trabecular Bone Structure

Embodiments of the present disclosure can also use spectral CBCT to generate a trabecular bone score (TBS) or other suitable metric to characterize trabecular bone structure for identified bone portions of the scanned volume.

Spectral radiography obtains image content by exposing the patient to x-ray radiation over a range of wavelengths, enabling particular characteristics of the object to be measured using additional information. As types of spectral radiography that provide at least a measure of 3-D information, "spectral CBCT" systems or methods, as well as spectral tomosynthesis methods and apparatus acquire volume image content by scanning the patient using more than a single emission spectrum to acquire multiple images. With respect to FIG. 1, the x-ray source that generates focal spot 100 is energizable to direct, through a volume, x-ray radiation of at least a first wavelength and a second wavelength. The imaging detector is disposed to generate image content according to acquired energy of at least the first and second wavelengths and, alternately, of more than two wavelengths.

Dual-energy radiography, as described previously for BMD characterization, is one mode of spectral radiography that is available for either 2-D or 3-D imaging. The CBCT system equipped to provide dual-energy scanning can operate by scanning the patient with x-ray energy over a first spectrum and scanning the patient with x-ray energy over a second spectrum. This imaging mode can use two separate scans, one at each energy spectrum, or can alternate exposure over each spectrum in a single scan of the patient. Another imaging mode for spectral radiography uses a photon-counting detector. This type of detector allows binning or other methods for distinguishing and recording emitted energy according to wavelength.

The Applicants have recognized the value of spectral radiography, in a number of imaging modes, for acquiring information related to trabecular bone structure. The combined trabecular bone score (TBS) and BMD data, acquired using spectral radiography imaging, can provide the practitioner with a more accurate characterization of bone tissue than has been available previously.

Figure 7:
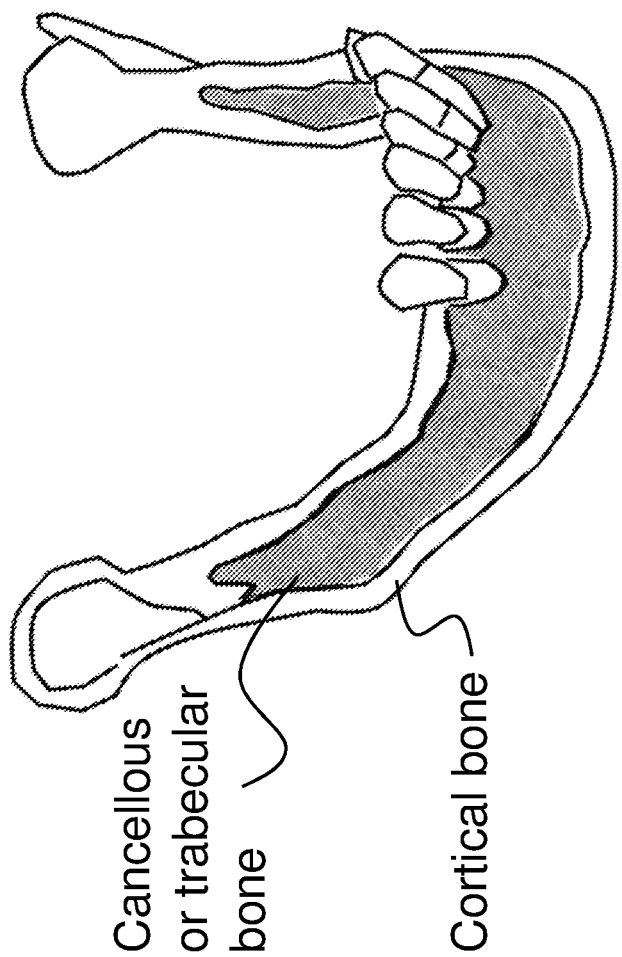
FIG. 7 is a schematic diagram of the lower jaw showing general locations of cortical and trabecular bone.

As shown schematically in FIG. 7, two different types of bone structure that support the teeth are of particular interest for dental imaging applications: cortical bone and trabecular bone. Cortical bone is exterior to the trabecular and is compact and of significantly higher density than the trabecular. Among its functions, cortical bone forms the continuous outer and inner plates surrounding the trabecular bone. The trabecular bone, largely responsible for overall strength and flexibility of the structural attachment of the teeth, has a complex, honeycomb-like structure formed of tiny, irregularly spaced lattice-shaped units (trabeculae).

Trabecular bone structure is quantified over a volume of bone in terms of a trabecular bone score (TBS). By comparison with BMD metrics that average bulk density values of pixels/voxels within imaged bone, TBS metrics characterize local bone structure as evidenced by bone texture. In TBS imaging techniques, local differences in density of the bone can be measured to determine characteristics such as thickness and frequency of the cell-like cavities in 2D or 3D dimensions.

For measurement of trabecular bone, variations along the bone mass can be sampled from individual pixels/voxels outward, using localized measurement of trabecular thickness and gradient features to provide, among other aspects, a measure of bone strength and an assessment of relative robustness of the bone for ability to withstand stress and weight, for support of implants, and for other characteristics.

Figure 8:
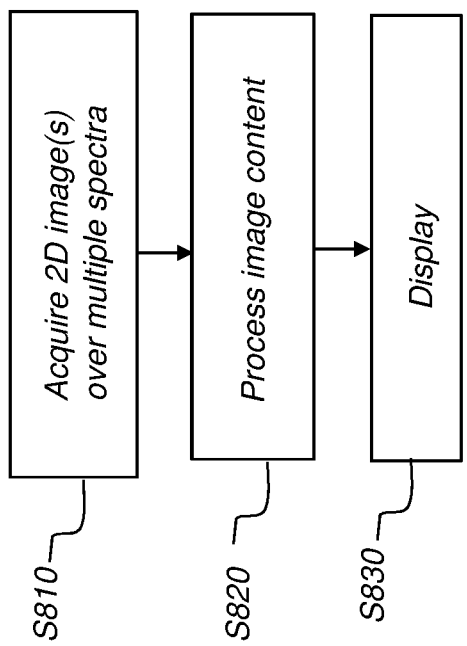
FIG. 8 is a logic flow diagram that shows a sequence for radiographic imaging to characterize trabecular bone structure.

TBS can be evaluated using 2D or 3D imaging methods. The logic flow diagram of FIG. 8 shows a sequence for radiographic imaging to characterize trabecular bone structure. In an image acquisition step S810, one or more 2D x-ray projection images is acquired at two or more frequencies. As noted previously, the projected radiation can be broadband x-ray, with radiation spanning a range of frequencies of 25 nm or greater and a photon-counting detector, allowing the use of a single exposure to provide multiple wavelength bands. Alternately, the projected radiation can be generated by energizing an x-ray source that directs a first wavelength, followed by a second wavelength and, alternately, additional wavelengths to generate multiple images, one for each wavelength. For a volume imaging apparatus such as a spectral CBCT system, step S810 can acquire a set of individual 2D projection images over a range of angles with respect to the imaged subject.

A processing step S820 is then carried out by the computer or other control logic processor that performs image processing on the acquired image content. For a 2D radiographic apparatus, this processing can provide standard techniques for addressing problems of noise and scatter, for example. For a tomosynthesis or 3D apparatus, processing can generate the corresponding tomosynthesis image, with enhanced depth information, or a full 3D volume image. Processing can then analyze the acquired and processed image in order to characterize the bone structure of the imaged jaw or other anatomy.

A display step S830 then reports the computed TBS measurement by display, such as on the display monitor provided with the imaging system and in signal communication with the computer or other control logic processor. The calculated results can also be stored or transmitted to another processor for further evaluation and analysis.

The overall process described with reference to the logic flow diagram of FIG. 8 can be used for intraoral imaging, in which the detector is positioned within the mouth of the patient, or extraoral imaging, in which the detector is external to the patient.

TBS assessment from image content can measure texture of the trabecular bone. Texture measurements evaluate the bone using metrics for localized bone thickness and texture, using algorithms and techniques for texture measurement known to those skilled in the imaging arts.

Figure 9:
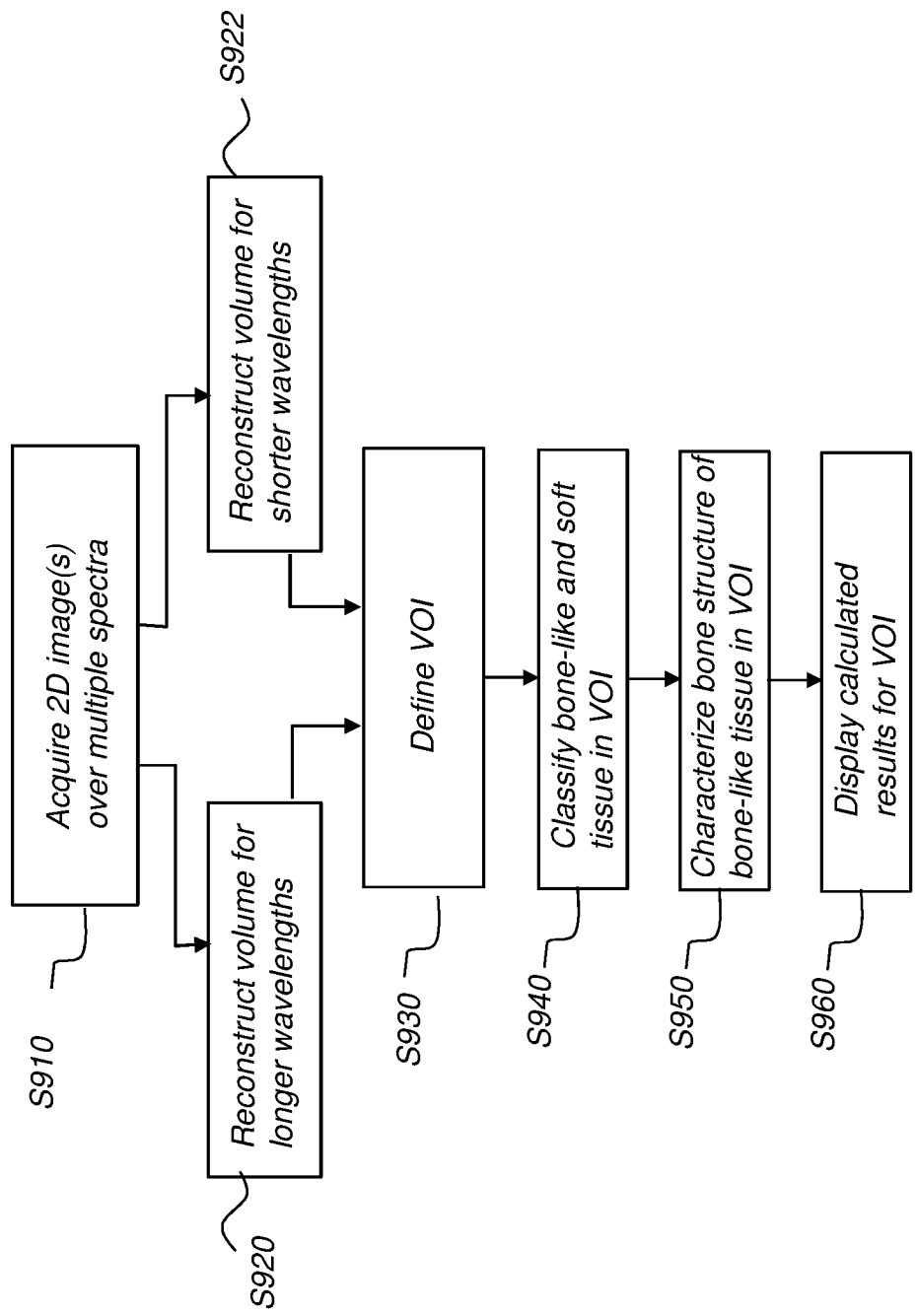
FIG. 9 is a logic flow diagram that shows a sequence for trabecular bone structure characterization using spectral CBCT with a photon-counting detector according to an embodiment of the present disclosure.

Referring to the logic flow diagram of FIG. 9, there is shown a sequence for trabecular bone structure characterization using spectral CBCT with a photon-counting detector according to an embodiment of the present disclosure. In a scan step S910, the patient is scanned with energy applied over a range of x-ray wavelengths. The detector acquires the image data, binned or otherwise collected according to particular wavelength bands. 2D projection image content for at least a first wavelength band and a second wavelength band are obtained and can be used to form respective reconstructed images in reconstruction steps S920 and S922. Projection images for more than two wavelength bands can be acquired, with corresponding volume reconstruction for each additional wavelength band. Alternately, a single volume image can be provided as a result of image reconstruction, combining results from the 2D image content acquired from multiple exposures at different wavelengths.

A VOI definition step S930 then defines the VOI from the reconstructed image content. The VOI represents the bone material of interest for trabecular bone structure and identifies identical voxels or regions of voxels in each reconstruction.

A classification step S940 classifies bone tissue from the reconstructed data in each reconstruction. Classification step S940 can use conventional automated or operator-assisted segmentation utilities, for example. A characterization step S950 then processes the VOI content to determine the bone texture data indicative of trabecular bone structure and provide the corresponding TBS quantification. In addition, characterization step S950 can also provide BMD data, using suitable steps from procedures outlined in FIG. 5 or 6, for example. At the conclusion of this processing sequence, a display step S960 displays calculated results indicative of the trabecular bone structure, BMD, or both. This data can be stored and can be transmitted to other systems or processes.

It can be appreciated that the basic sequence of FIG. 9 can be adapted for spectral tomosynthesis as well as for spectral CBCT. A subset of the FIG. 9 processing can also be used to obtain bone quality information for 2-D imaging using spectral radiography.

Figure 10:
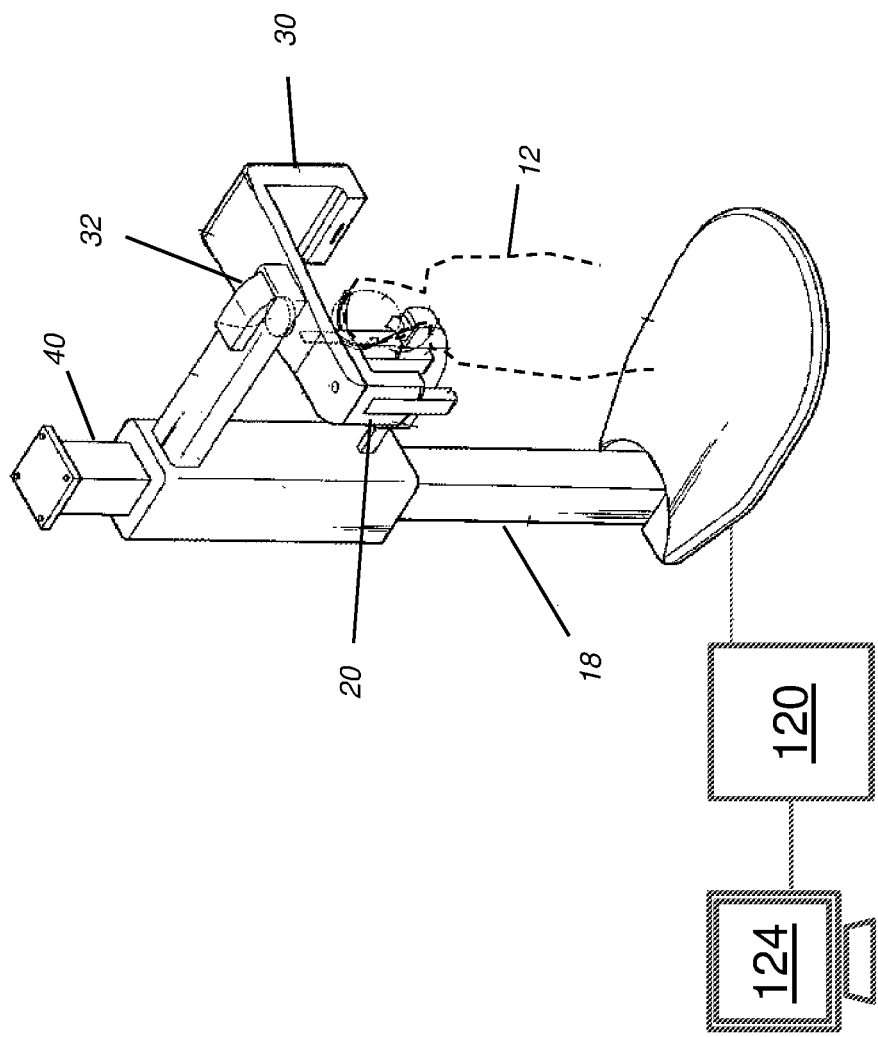
FIG. 10 shows an embodiment of an extraoral apparatus for spectral imaging.

By way of example, FIG. 10 shows an embodiment of a spectral CBCT imaging apparatus 40 for extraoral imaging. A telescopic column 18 is adjustable for height of the subject. The patient 12 or other subject, shown in phantom outline, is positioned between an x-ray source 30 and an x-ray imaging detector 20. X-ray imaging detector 20 rotates on a rotatable mount 32 in order to position detector 20 for obtaining the exposure from source 30 at each of a number of angles. Control logic processor 120, in signal communication with apparatus 40, provides the needed control and imaging processing functions for TBS calculation.

FIG. 11 shows an embodiment of an intraoral apparatus 50 for spectral imaging. Detector 20 is held in the mouth of the patient, such as by using a frame with bite element (not shown). Source 30 is directed toward detector 20, such as using an alignment mechanism (not shown).

Consistent with at least one exemplary embodiment, exemplary methods/apparatus can use a computer program with stored instructions that perform on image data that is accessed from an electronic memory. As can be appreciated by those skilled in the image processing arts, a computer program of an exemplary embodiment herein can be utilized by a suitable, general-purpose computer system, such as a personal computer or workstation. However, many other types of computer systems can be used to execute the computer program of described exemplary embodiments, including an arrangement of one or networked processors, for example.

A computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine-readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and/or processes that are well known. It will be further understood that exemplary computer program product embodiments herein may embody algorithms and/or processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

Exemplary embodiments according to the present disclosure can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/exemplary embodiments, such feature can be combined with one or more other features of the other implementations/exemplary embodiments as can be desired and advantageous for any given or particular function. The term "a" or "at least one of" is used to mean one or more of the listed items can be selected. The term "about" indicates that the value listed can be somewhat altered, as long as the alteration does not result in nonconformance of the process or structure to the illustrated exemplary embodiment. Further, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for characterizing dental bone structure for a patient, the method executed at least in part on a computer and comprising:
 a) acquiring one or more 2D x-ray projection images of a volume including the dental bone structure, wherein image content is acquired at two or more spectral frequencies;
 b) processing the acquired x-ray image content to calculate one or more metrics that characterize the dental bone structure within the imaged volume; and
 c) displaying the one or more calculated metrics.

2. The method of claim 1 wherein acquiring the one or more x-ray projection images comprises using an extraoral radiation detector.

3. The method of claim 1 wherein acquiring the one or more x-ray projection images comprises using an intraoral radiation detector.

4. The method of claim 1 wherein processing the acquired x-ray image content comprises reconstructing a tomosynthesis image.

5. The method of claim 4 further comprising identifying a volume of interest.

6. The method of claim 1 wherein processing the acquired x-ray image content comprises reconstructing a 3D tomographic image.

7. The method of claim 1 wherein processing the acquired x-ray image content comprises calculating the one or more metrics from the one or more 2D projection images.

8. The method of claim 1 wherein processing the acquired x-ray image content comprises calculating bone mineral density.

9. The method of claim 1 wherein processing the acquired x-ray image content comprises calculating a trabecular bone score.

10. The method of claim 1 wherein processing the acquired x-ray image content further comprises identifying bone-like tissue.

11. A method for characterizing bone structure for a patient, the method executed at least in part on a computer and comprising:
 a) acquiring a plurality of x-ray projection images of a volume at two or more spectral frequencies;
 b) reconstructing at least a portion of the volume using the plurality of x-ray projection images;
 c) identifying a volume of interest (VOI) within the reconstructed portion of the volume;
 d1) classifying bone-like tissue and soft tissue within the VOI;
 d2) determining an indication of local spectral distribution of x-rays in the reconstructed VOI using the classified soft tissue in the reconstructed VOI;
 e) calculating, from the indication of the local spectral distribution of x-rays and the classified bone-like tissue in the reconstruction VOI, at least one of bone density and bone structure of bone-like tissue in the portion of the volume; and
 f) displaying calculated values for at least one of bone density and bone structure of bone-like tissue in the portion of the volume.

12. The method of claim 11 wherein the one or more projection images are acquired on an intraoral detector.

13. The method of claim 11 wherein the one or more projection images are acquired on an extraoral detector.

14. The method of claim 11 wherein calculating defines a trabecular bone score of a dental bone structure for the patient.

15. The method of claim 11 wherein calculating defines a bone mineral density measurement of a dental bone structure for the patient.

16. The method of claim 11 wherein acquiring the one or more x-ray projection images comprises using a tomosynthesis imaging system.

17. The method of claim 11 wherein acquiring the one or more x-ray projection images comprises using a computed tomography imaging system.

18. The method of claim 11 wherein acquiring the one or more x-ray projection images comprises using a cone beam computed tomography imaging system.

19. The method of claim 11 wherein classifying comprises using an image segmentation algorithm.

20. The method of claim 11 wherein the two or more spectral frequencies differ by more than 25 nm.

21. A dental imaging apparatus comprising:
  a) an x-ray source that is energizable to direct, through a volume, x-ray radiation at least at a first wavelength and at a second wavelength;
  b) an imaging detector that is disposed to generate image content according to acquired energy of the at least the first and second wavelengths;
  c) a processor that is programmed according to stored instructions to:
    (i) acquire a plurality of x-ray projection images of the volume at the at least first and second wavelengths;
    (ii) reconstruct at least a portion of the volume using the plurality of x-ray projection images;
    (iii) identify a volume of interest (VOI) within the reconstructed portion of the volume;
    (iv) classify bone-like tissue and material of known composition within the reconstructed VOI;
    (v) calculate, from reconstruction data and a known material density of the material of known composition, at least one of bone density and bone structure of bone-like tissue in the portion of the volume; and
  d) a display that is in signal communication with the processor and is configured to display the calculated values for the at least one of bone density and bone structure of the bone-like tissue in the portion of the volume from the processor.

22. The apparatus of claim 21 wherein the second wavelength is more than 25 nm from the first wavelength.

23. The apparatus of claim 21 wherein the detector is a photon-counting detector, wherein the material of known composition is soft tissue adjacent the bone-like tissue in the reconstructed VOI.

* * * * *